(12) United States Patent
Brown et al.

(10) Patent No.: US 8,536,626 B2
(45) Date of Patent: Sep. 17, 2013

(54) ELECTRONIC PH SENSOR DIE PACKAGING

(75) Inventors: Gregory C. Brown, Chanhassen, MN (US); Curtis H. Rahn, Plymouth, MN (US)

(73) Assignee: Honeywell International Inc., Morristown, NJ (US)

( * ) Notice: Subject to any disclaimer, the term of this patent is extended or adjusted under 35 U.S.C. 154(b) by 0 days.

(21) Appl. No.: 13/096,710

(22) Filed: Apr. 28, 2011

(65) Prior Publication Data
US 2012/0273845 A1 Nov. 1, 2012

(51) Int. Cl.
*G01N 27/414* (2006.01)

(52) U.S. Cl.
USPC ............ 257/253; 257/414; 204/416

(58) Field of Classification Search
CPC ...................................... G01N 27/44
USPC ........... 257/253, 414; 204/416–418, 403.01, 204/401.15, 433, 435; 324/438
See application file for complete search history.

(56) References Cited

U.S. PATENT DOCUMENTS

| | | | |
|---|---|---|---|
| 4,056,681 A | | 11/1977 | Cook, Jr. |
| 4,133,735 A | * | 1/1979 | Afromowitz et al. ......... 204/406 |
| 4,409,980 A | | 10/1983 | Yano et al. |
| 4,889,612 A | * | 12/1989 | Geist et al. .................... 204/416 |
| 5,068,205 A | | 11/1991 | Baxter et al. |
| 5,221,456 A | * | 6/1993 | Benton et al. ................ 204/416 |
| 6,117,292 A | | 9/2000 | Ahmad et al. |
| 6,875,328 B2 | | 4/2005 | Tominaga et al. |
| 2002/0087057 A1 | | 7/2002 | Lovejoy et al. |
| 2003/0047453 A1 | | 3/2003 | Barben, II et al. |
| 2004/0213820 A1 | | 10/2004 | Yokoi et al. |
| 2005/0129580 A1 | * | 6/2005 | Swinehart et al. ............ 422/100 |
| 2005/0170347 A1 | | 8/2005 | Miyahara et al. |
| 2006/0029955 A1 | | 2/2006 | Guia et al. |
| 2008/0012049 A1 | * | 1/2008 | Niwa et al. .................... 257/253 |
| 2009/0108831 A1 | | 4/2009 | Levon et al. |
| 2010/0181210 A1 | * | 7/2010 | Qin et al. .................... 205/777.5 |
| 2010/0301398 A1 | * | 12/2010 | Rothberg et al. ............. 257/253 |

FOREIGN PATENT DOCUMENTS

| | | | |
|---|---|---|---|
| EP | 0 840 369 A1 | | 5/1998 |
| GB | 2126786 A | * | 3/1984 |
| WO | 9613056 | | 5/1996 |
| WO | 98/21572 A1 | | 5/1998 |
| WO | 2009082516 A2 | | 7/2009 |

OTHER PUBLICATIONS

Annual Report, "Optical Fiber Sensor Technologies for Efficient and Economical Oil Recovery," DOE/BC/15167-1, DOE Award No.—DE-FG26-98BC15167, 101 pages, Oct. 1, 2000-Sep. 30, 2001.

(Continued)

*Primary Examiner* — Cuong Q Nguyen
*Assistant Examiner* — Yosef Gebreyesus
(74) *Attorney, Agent, or Firm* — Shumaker & Sieffert, P.A.

(57) ABSTRACT

A pH sensor is provided. The pH sensor comprises a substrate and an ion sensitive field effect transistor (ISFET) die comprising an ion sensing part that responds to pH, wherein the ISFET die is located over the substrate. The pH sensor also comprises a protective layer formed over at least a portion of an outer surface of the ISFET die and at least a portion of the substrate. Further, the pH sensor comprises a cover member mechanically coupled to the protective layer, wherein the cover member houses the ISFET die and the substrate, and wherein the cover member defines an opening proximate to the ion sensing part.

15 Claims, 5 Drawing Sheets

(56) References Cited

OTHER PUBLICATIONS

Knechtel, Glass Frit Bonding: An Universal Technology for Wafer Level Encapsulation and Packaging, Microsystem Technology, vol. 12, No. 1-2, 6 pages, 2005.

European Search Report dated Mar. 12, 2013, for counterpart EP Application No. 12157017.0, 3 pages.
Examination Report from counterpart EP Application No. 12 157 017.0, mailed Mar. 27, 2013, 8 pages.

* cited by examiner

ELECTRONIC PH SENSOR DIE PACKAGING

STATEMENT REGARDING FEDERALLY SPONSORED RESEARCH OR DEVELOPMENT

This invention was made with Government support under Government Contract No. N00014-10-1-0206 awarded by MBARI/Office of Naval Research. The Government has certain rights in the invention.

TECHNICAL FIELD

The disclosure relates to pH sensors, such as electronic pH sensors.

BACKGROUND

Some ion sensitive field effect transistors (ISFETs) are used to detect a pH level of a media in which the ISFET is immersed. One type of electronic pH sensor is a silicon micro-electro-mechanical system (MEMS) device that utilizes a metal-oxide-semiconductor field-effect transistor (MOSFET) structure in combination with a reference electrode to detect pH.

SUMMARY

In one example, a pH sensor is provided that comprises a substrate and an ion sensitive field effect transistor (ISFET) die comprising an ion sensing part that responds to pH, wherein the ISFET die is located over the substrate. The pH sensor also comprises a protective layer formed over at least a portion of an outer surface of the ISFET die and at least a portion of the substrate. Further, the pH sensor comprises a cover member mechanically coupled to the protective layer, wherein the cover member houses the ISFET die and the substrate, and wherein the cover member defines an opening proximate to the ion sensing part.

In another example, a sensor device comprises a substrate and a field effect transistor (FET) die mounted over the substrate via a frit material. The sensor device also comprises a protective layer formed at least partially over an outer surface of the FET die and at least partially over the substrate. Further, the sensor device comprises at least one wire that is bonded to the FET die at a first end, wherein at least a portion of the wire is embedded in the frit material.

In a further example, a method of manufacturing a sensor device is provided. The method comprises bonding a first end of a wire to a first side of a field effect transistor (FET) sensing die and embedding at least a portion of the wire in a frit material. The method further comprises attaching a substrate to the first side of the FET sensing die via the frit material and attaching a cap over the substrate by at least applying a frit layer between the substrate and the cap. The method also comprises forming a protective layer over at least a portion of the cap and at least a portion of the FET sensing die.

The details of one or more examples of the disclosure are set forth in the accompanying drawings and the description below. Other features, objects, and advantages of the disclosure will be apparent from the description and drawings, and from the claims.

BRIEF DESCRIPTION OF DRAWINGS

In accordance with common practice, the various described features are not drawn to scale and are drawn to emphasize features relevant to the present disclosure. Like reference characters denote like elements throughout the figures and text.

DETAILED DESCRIPTION

Some electronic pH sensor devices have a silicon (Si) micro-electro-mechanical system (MEMS) device and a field effect transistor (FET) structure. An example of such a pH sensor device may comprise an ion sensitive field effect transistor (ISFET). An ion sensitive part of the ISFET may be exposed to a media of interest. When exposed to the media, a gate voltage across the ISFET may be related to a pH of the media. The gate voltage of the ISFET device is a difference between a FET junction voltage and a voltage of a reference electrode that is also immersed in the media. The FET gate voltage correspondingly changes as the pH of the media changes, providing an electronic signal indicative of the pH of the media.

In some applications, the pH sensor device may be exposed to an environment that is corrosive or deleterious to at least one component of the pH sensor device, which may affect the performance and integrity of the pH sensor device. Additionally, the accuracy of the pH measurements may drift over time. For example, in high pressure environments, a pH sensor device may be strained under the high pressure. Furthermore, numerous pressure cycles may lead the pH sensor device to provide inaccurate readings or other sensor errors. In other examples, the composition of the media may corrode materials in the pH sensor device, for example, salt in seawater.

Techniques of the present disclosure provide a pH sensor device that may be more robust in high pressure or corrosive environments than some conventional pH sensor devices. For example, a pH sensor device can comprise an ISFET die that may be mounted to a sensor package to improve strain isolation for the ISFET die. In one example, a protective layer is formed over at least a portion of a pH sensor assembly, for example, at least in areas that may be exposed to the media. The protective layer may help reduce corrosion of portions of the sensor assembly which the protective layer covers compared to examples in which these portions of the sensor assembly are ordinarily exposed to the media. In some examples, a frit material is used to encapsulate wires in the pH sensor to improve stress isolation. The pH sensor device may retain a relatively high accuracy over an extended period of time compared to conventional pH sensor devices. For example, the pH sensor device may maintain less than a maximum drift over 5 to 10 years, or over any other time period.

Figure 1:
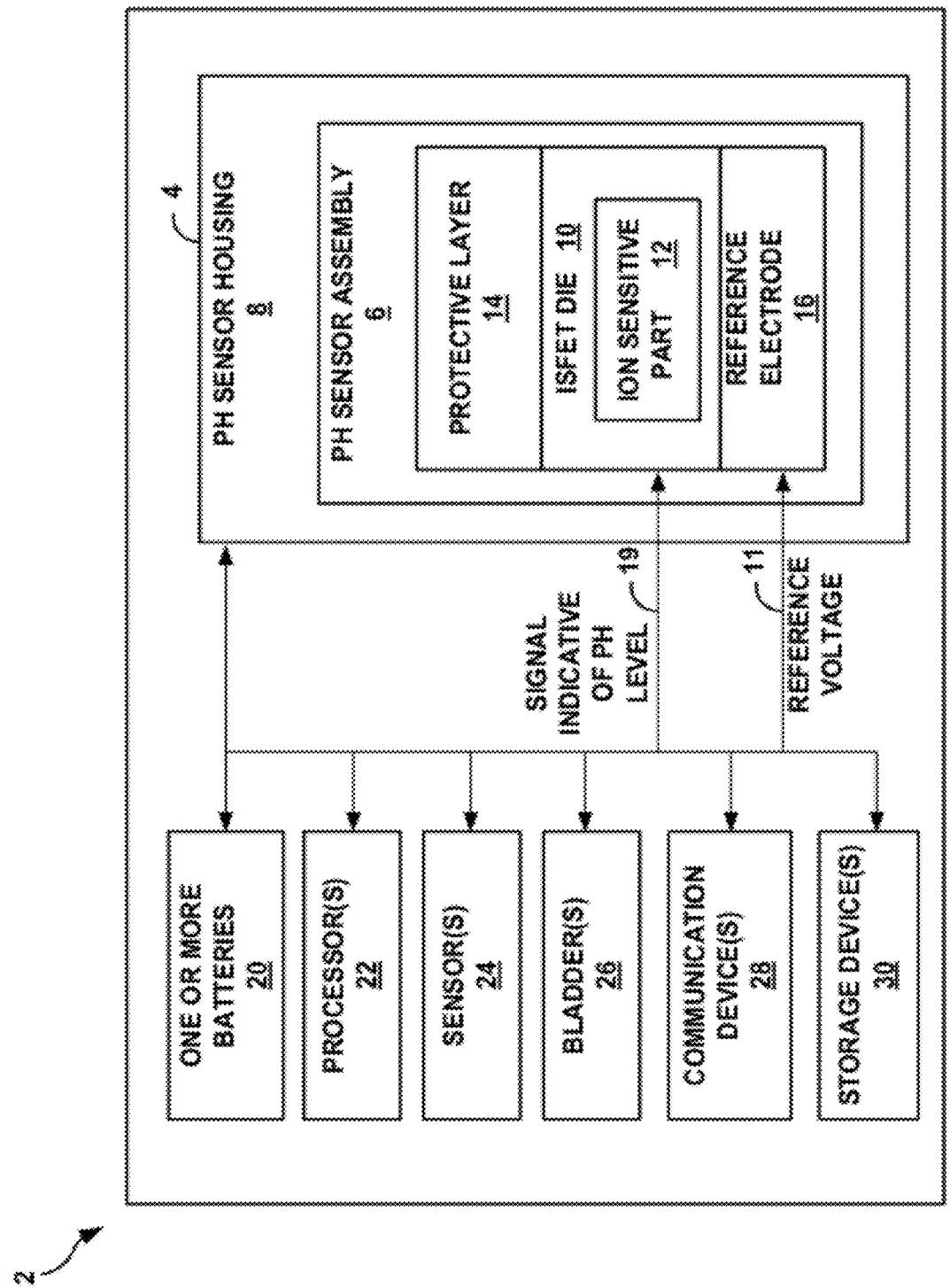
FIG. 1 is a block diagram illustrating one example of a sensor device comprising a pH sensor, in accordance with one or more aspects of the present disclosure.

FIG. 1 is a block diagram illustrating one example of a sensor device 2 comprising a pH sensor 4, in accordance with one or more aspects of the present disclosure. In one example, pH sensor 4 measures the amount of hydrogen ion concentration of a solution (commonly denoted as "pH"). Sensor device 2 may further comprise one or more batteries 20, one or more processors 22, one or more one sensors 24, one or more bladders 26, or more communication devices 28, and one or more storage devices 30. Other examples of sensor device 2 may include only some of these components, or other additional components as well.

In one example, pH sensor 4 may comprise a pH sensor assembly 6 that is at least partially encased in a pH sensor housing 8. In one example, pH sensor assembly 6 may comprise an ISFET die 10 including an ion sensitive part 12. A protective layer 14 may be formed at least partially on ISFET die 10. Additionally, the pH sensor assembly 6 may further comprise a reference electrode 16. One example of pH sensor 4 is more fully described in FIG. 2, discussed below.

In one example, pH sensor 4 is configured such that at least a portion of ion sensitive part 12 and reference electrode 16 may be exposed to a media, for example, a fluid, in order to determine the pH of the media. In one example, protective layer 14 covers a portion of pH sensor assembly 6 that is not intended to be exposed to the media. In one example, protective layer 14 may be approximately chemically inert in the media. For example, the media that sensor device 2 is immersed in does not corrode protective layer 14. As an example, the media may not substantially leach ions out of protective layer 14.

In one application, sensor device 2 may be an oceanographic buoy. An oceanographic buoy may be a type of weather buoy that measures parameters of the ocean or other body of water. Such parameters may include, for example, salinity, temperature, currents, tides, pH, position, the presence of bioluminescence, etc. Sensors 24 may be used to measure one or more of these, or other, parameters. For example, sensors 24 may include a thermometer, a camera device, a hydrometer, or the like. In such an application, pH sensor 4 may be used to measure the pH of sea or ocean water. For example, pH sensor 4 can be configured such that at least a portion of ion sensitive part 12 and a portion of reference electrode 16 are exposed to the sea or ocean water. In one example, sensing device 2 measures ocean pH, which may be used for detecting changes in ocean $CO_2$ levels.

Exposing ion sensitive part 12 to the media (e.g., ocean water) may allow pH sensor 4 to detect a change in the pH level of the media. In some examples, pH sensor 4 is configured to generate a voltage that changes as a function of the pH level of the media. For example, in one example, a gate of ISFET die 10 may be ion sensitive part 12, which is sensitive to an ion solution. Thus, the gate voltage of ISFET die 10 depends on the pH of the solution that sensor device 2 is in. Changes in the pH of the media in which the ion sensitive part 12 is exposed causes potential changes in ISFET die 10. A reference voltage 11 drives ISFET die 10 in order to maintain the current through ISFET die 10 at an approximately constant level. When the pH changes, the bias point of ISFET die 10 also changes. Reference voltage 11 is correspondingly changed to keep the current in ISFET die 10 approximately constant. This change in voltage of reference voltage 11 is related to a change in the pH of the media. ISFET die 10 outputs a signal indicative of pH level 19. In some examples, the signal related to pH level 19 is provided to one or more processors 22. In another example, the signal indicative of the pH level 19 is stored in one or more storage devices 30. As discussed in further detail below, in addition or instead to locally storing the signal indicative of pH level 19, the signal indicative of pH level 19 is transmitted to a device external to sensor device 2.

In some examples, sensor device 2 may be deployed in an ocean to take measurements over a period of time. Sensor device 2 may be released into the ocean at a depth below the ocean's surface (e.g., approximately 1000 meters below the ocean's surface). In order for sensor device 2 to ascend or descend, battery 20 may pump water out of or into bladder 26 to increase or decrease the buoyancy of sensor device 2, respectively. Once deployed, sensor device 2 may take measurements of ocean parameters while slowly rising to the surface. In some examples, rising to the surface from a depth of 1000 meters may take three to six weeks. However, other time periods are contemplated.

As measurements are taken, the measurements may be stored in storage device 30. Once at or near the surface, sensor device 2 may transmit the measurements saved in storage device 30 using one or more communication devices 28. For example, sensor device 2 may report this telemetry data to a research center via a satellite radio link.

Once the transmission of the measurements is complete, battery 20 may pump water back into bladder 26 so that sensor device 2 submerses for another time period. This cycle may be repeated again, for example, over years or until the one or more batteries 20 are drained. Over these repeated cycles, components of sensor device 2 may be subject to corrosion or strains due to long term exposure to the media, to high pressures, and to a plurality of pressure cycles. Examples of pH sensor 4 according to this disclosure may be more robust than traditional pH sensors due to, e.g., protective layer 14 and/or other features described in further detail below with respect to FIG. 2. In applications such as oceanographic research, extended unattended operation of pH sensor 4 over a period of several years may be achieved with higher accuracy relative to conventional pH sensors. In one example, pH is measured to an accuracy of approximately 0.02%. In other examples, other accuracies are achieved.

The one or more processors 22 may be configured to implement functionality and/or process instructions for execution in sensor device 2. Processors 22 may be capable of processing instructions stored on storage devices 30. Processors 22 may include any one or more of a microprocessor, a controller, a digital signal processor (DSP), an application specific integrated circuit (ASIC), a field-programmable gate array (FPGA), or discrete logic circuitry. The functions attributed to processors 22 described herein may be embodied in a hardware device via software, firmware, hardware or any combination thereof.

Storage devices 30 may also include one or more computer-readable storage media. Storage devices 30 may be configured to store sensor readings from pH sensor 4 and sensors 24. Storage devices 30 may further be configured for long-term storage of information. In some examples, storage devices 30 may include non-volatile storage elements. Examples of such non-volatile storage elements may include, but are not limited to, magnetic hard discs, optical discs, floppy discs, flash memories, or forms of electrically programmable memories (EPROM) or electrically erasable and programmable (EEPROM) memories. In some examples, sensor device 2 comprises one storage device 30.

In some examples, sensor device 2 may utilize one or more communication devices 28 to wirelessly communicate with an external device or other networked computing device. Examples of communication devices 28 may include wireless devices (e.g., a cell phone, radio, and the like), satellite communications devices, or radar devices. One or more communication devices 28 may comprise a network interface card for communicating with processors 22 or for receiving data from storage devices 30. In one example, one or more communication devices 28 may comprise an Ethernet card, configured to communication over, for example, Ethernet, transmission control protocol (TCP), Internet protocol (IP), asynchronous transfer mode (ATM), or other network communication protocols. In other examples, one or more communication device 28 may be an optical transceiver, a radio frequency transceiver, or any other type of device that can send and receive information. In one example, communication device 28 may comprise an antenna.

Examples of such communication devices 28 may include Bluetooth®, 3G, WiFi®, very high frequency (VHF), and ultra high frequency (UHF) radios. Communication devices 28 may also be configured to connect to a wide-area network such as the Internet, a local-area network (LAN), an enterprise network, a wireless network, a cellular network, a telephony network, a Metropolitan area network (e.g., Wi-Fi, WAN, or WiMAX), one or more other types of networks, or a combination of two or more different types of networks (e.g., a combination of a cellular network and the Internet).

Sensor 2 may include one or more batteries 20, which may be rechargeable in some examples and provide power to sensor device 2. One or more batteries 20 may be made from nickel-cadmium, lithium-ion, or any other suitable material. In one example, one or more batteries 20 provide reference voltage 11 to pH sensor 4.

Figure 2:
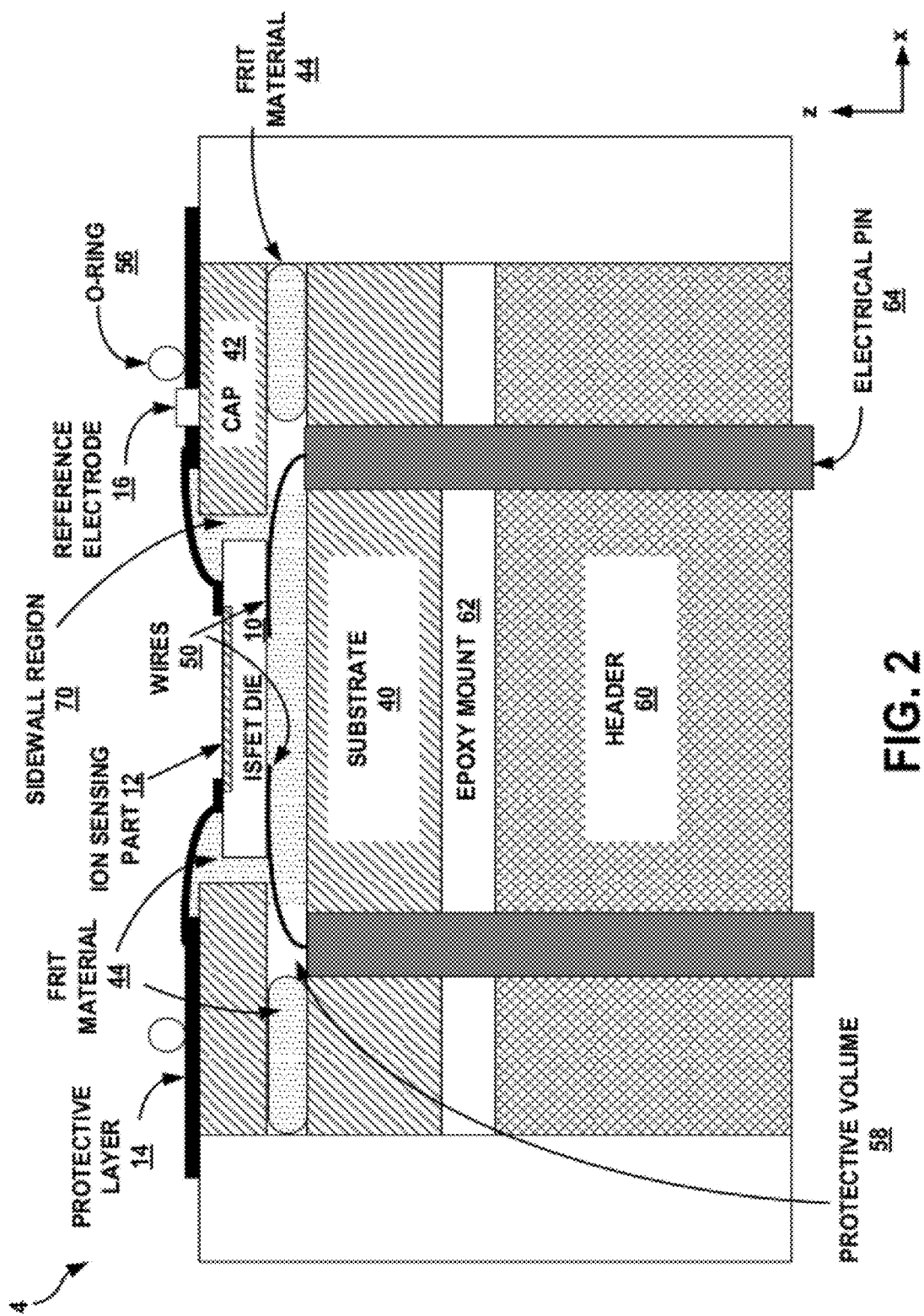
FIG. 2 is a block diagram illustrating one example of a pH sensor comprising a protective layer, in accordance with one or more aspects of the present disclosure.

FIG. 2 is a block diagram illustrating one example of a pH sensor 4 comprising a protective layer 14, in accordance with one or more aspects of the present disclosure. In this example, pH sensor 4 comprises an ISFET die 10 mounted on a substrate 40. As discussed herein, components of pH sensor 4, including ISFET die 10, as similar to like components described with respect to FIG. 1.

As shown in FIG. 2, pH sensor 4 comprises a header 60, to which the pH sensor assembly may be mounted. In one example, header 60 comprises a glass-filled plastic. In some examples, header 60 is configured to support pH sensor 4 for a particular application, e.g., implementation in a particular sensing device. For example, header 60 can be configured to substantially not corrode in the media of interest over a lifetime of a sensing device in with pH sensor 4 is installed.

An example ISFET die 10 is comprised of silicon (Si) and an ion sensitive part that may be used for sensing pH, such as ion sensing part 12 (FIG. 1). In other examples, ISFET die 10 is another type of die that may be used to detect pH of a solution. In one example, a portion of ISFET die 10 may be exposed to seawater and pH sensor 4 may generate an electrical signal indicative of a pH of the seawater.

In the example shown in FIG. 2, substrate 40 supports ISFET die 10 and defines through-holes for one or more electrical pins 64. Examples of suitable materials for substrate 40 include, but are not limited to, ceramic, Si, silicon nitride ($Si_3N_4$), sapphire, diamond, silicon on diamond (SOD), silicon on insulator (SOI), or any other suitable substrate material. In examples where substrate 40 is ceramic, substrate 40 may be comprised of, but not limited to, a high density alumina, alumina nitride (AlN), or silicon nitride ($Si_3N_4$). In other examples, substrate 40 may be composed of other materials, such as Teflon, or combinations thereof. In some examples, substrate 40 may be approximately between 0.1 to 100 micrometers (μm) thick. In other examples, substrate 40 may be other thicknesses.

One or more wires 50 provide an electrical connection between ISFET die 10 and circuitry external to die 10. As shown in FIG. 2, one or more wires 50 may be wire bonded to an underside of ISFET die 10 and to at least one electrical pin 64. One example of wires 50 may comprise gold (Au) wire with an approximate thickness of 2 mm or less. In other examples, wires 50 may be composed of other materials, such as aluminum, and may have other thicknesses.

As shown in FIG. 2, pH sensor 4 comprises cap 42, which is positioned around ISFET die 10. In one example, a cap 42 may be at least partially bonded to substrate 40. In some examples, cap 42 is referred to as a cap substrate and substrate 40 is referred to as a base substrate. Cap 42 may include a cut-out for ISFET die 10. Examples of the composition of cap 42 may include ceramic materials such as a high density alumina, AlN, or $Si_3N_4$, Si, sapphire, diamond, SOD, SOI, or any other suitable substrate materials or combinations thereof. In one example, cap 42 comprises the same composition as substrate 40. In other examples, cap 42 comprises a different material than substrate 40.

In one example, substrates 40 and 42 provide rigid support for ISFET die 10, which is mounted in substrates 40, 42, so that repeatable strains due to changes of temperature and pressure are reduced. In some examples of pH sensor 4, a top surface (e.g., a greatest z-axis dimension, where x-z axes are shown in FIG. 2 for ease of description only) of ISFET die 10 may be nearly flush with a top surface of cap 42 or a top surface of protective layer 14, which aids in flowing media by ion sensitive part 12. In other examples, as shown in FIG. 2, a top surface of ISFET die 10 is recessed within an opening defined by cap 42. In one example, protective layer 14 is approximately parallel with substrate 40.

Additionally, in some examples, pH sensor 4 further comprises a frit material 44, which may further reduce stress and strains to pH sensor 4, which in turn reduces the likelihood of failures and lessen errors. Frit material 44 may be a ceramic composition of a type suitable for use in wafer bonding processes. In one example, frit material 44 is a glass frit.

Frit material 44 may be formed in one or more of several locations in pH sensor 4. For example, frit material 44 may be formed in one or more of the areas between substrate 40 and cap 42, between ISFET die 10 and substrate 40, in a sidewall region 70 between ISFET die 10 and cap 42, on ISFET die 10, and on cap 42. In some examples, frit material 44 may range from 0.05 to approximately 10 mm thick. In one example, frit material 44 between cap 42 and substrate 40 may be up to approximately 6 mm thick. In another example, frit material 44 between ISFET die 10 and substrate 40 may be up to approximately 8 mm thick. In other examples, frit material 44 may be other thicknesses.

In some previous electric pH sensors, an ISFET die is either bonded directly to a substrate with epoxy or there are cavities between the ISFET die and the substrate. Exposing this type of pH sensor structure to a wide temperature range or to high pressures (for example, up to approximately 6 kilopounds per square inch (KSI)) may result in increased stress on and strain of the ISFET die due to the TCE mismatch between the substrate, epoxy, and ISFET die. This increased stress and strain may lead to increased errors in a pH output signal. In contrast, frit material 44 between ISFET die 10 and substrate 40 may reduce the effects of stress on ISFET die 10 by isolating ISFET die 10 from substrate 40.

Furthermore, in one example, a thermal coefficient of expansion (TCE) of frit material 44 is approximately the same as a TCE of ISFET die 10 (e.g., the same TCE as the silicon from which ISFET die 10 is formed). That is, frit material 44 and ISFET die 10 may expand and contract over temperature changes by approximately the same amount. By approximately matching the TCEs of frit material 44 and ISFET die 10, pH sensor 4 is subjected to less stress and strain (e.g., less strain from expansion of substrate 40 relative to ISFET die 10 or vice versa), which may improve the reliability and longevity of pH sensor 4.

In one example, one or more wires 50 may be embedded in frit material 44. Embedding one or more wires 50 in frit material 44 may provide increased protection of one or more wires 50 from temperature and pressure changes, as well as from leakage currents. In another example, wire bonds for one or more wires 50 to ISFET die 10 are embedded in frit material 44, which may provide a stable, rigid mount for one or more wires 50 to ISFET die 10.

In a further example, one or more wires 50 may also be bonded to one of the one or more electrical pins 64. A protective volume 58 may be formed around the wire bond between wire 50 and at least one electrical pin 64. In one example, protective volume 58 is a space over electrical pin 64 that does not have frit material 44 or any other bonding material. Frit material 44 may partially cover electrical pin 64 in some examples. In other examples, protective volume 58 comprises a gas, such as air, or is at least a partial vacuum. Protective volume 58 is further discussed in more detail below with respect to FIG. 4B.

In one application, pH sensor 4 may be exposed to a media in order to sense a pH of the media (e.g., seawater). Some media, such as seawater, may leach ions out of frit material 44 or cap 42, forming pores or potholes in frit material 44 or cap 42 that may lead to degradation of pH sensor 4. Because of this potential corrosion, protective layer 14 is formed on part of pH sensor 4. In one example, protective layer 14 is more inert in a given media (e.g., seawater) than frit material 44. In one example, protective layer 14 shields frit material 44 from long-term degradation due to exposure to salt water. In one example, protective layer 14 protects pH sensor 4 in a range of from a pH of approximately 1 to a pH of approximately 11.

Protective layer 14 may be a coating used as a primary barrier for across a portion of the surface of pH sensor 4. As shown in FIG. 2, protective layer 14 may be formed on cap 42 and part of ISFET die 10. Protective layer 14 may also be formed on a portion of frit material 44, such as frit material 44 in sidewall region 70. In one example, a portion of a header 60 (described in further detail below with respect to FIG. 4C), protective layer 14, an o-ring 56, and a portion of ISFET die 10 are exposed to the media of interest during operation of pH sensor 4.

In some examples, protective layer 14 may be a metallization layer. For example, protective layer 14 may be a metal-oxide protective coating, such as tantalum pentoxide ($Ta_2O_5$), tungsten pentoxide ($W_2O_5$), or any other metal-oxide or combinations thereof, or silicon nitride ($Si_3N_4$) that may be approximately inert in the media of interest over a selected time period (for example, up to 10 years). In addition or instead, protective layer 14 may be a diamond, such as a synthetic diamond, sapphire, or a ceramic material. In addition to or instead of the aforementioned examples, protective layer 14 may comprise a non-porous material.

Protective layer 14 may have a thickness such that protective layer 14 adheres to the surfaces of cap 42, ISFET die 10, and frit material 44, while having a relatively low probability of porosity compared to frit material 44 and/or cap 42. In one example, protective layer 14 may comprise multiple thin layers. Multiple thin layers may reduce the chance of developing pores in protective layer 14, which may lead to leaking and eventual degradation of pH sensor 4. In some examples, protective layer 14 may have a thickness of approximately 2,000 Angstroms (Å) to 10,000 Å. However, other thicknesses of protective layer 14 may be used in other examples. In some examples, protective layer 14 is of an approximately uniform thickness, while in other examples, the thickness of protective layer 14 varies.

In one example, protective layer 14 at least partially covers ion sensing part 12 and completely covers an outer surface of ISFET die 10 that is not ion sensing part 12. In another example, any exposed metallization (such as a test pad) on ISFET die 10 is covered by protective layer 14. In another example, protective layer 14 does not cover reference electrode 16. In yet another example, protective layer 14 may be formed over the entire surface of ISFET die 10. In some examples, any component, part, or aspect of pH sensor 4 that may be otherwise exposed to a media of interest, such as an electrical connection, may be covered by protective layer 14.

Protective layer 14 can have other configurations in other examples. For example, in one example, protective layer 14 may be conformal to the surfaces of cap 42, frit material 44, and ISFET die 10. In other examples, protective layer 14 is planar across the surfaces of cap 42, frit material 44, and ISFET die 10, such that the thickness of protective layer 14 varies in the x-axis direction. In another example, frit material 44 may not be in sidewall region 70, and thus is not directly covered by protective layer 14.

In some existing pH sensors, an o-ring is located on the ISFET die of the pH sensor. This o-ring seals a pH sensor assembly in a housing, wherein the housing exposes an ion sensitive part of the ISFET die. Temperature changes and high pressure expose the ISFET die to stresses from the o-ring or housing. In the existing pH sensors, these stresses may be compounded via cavities formed between the ISFET die and a substrate, because in such a structure, the ISFET die may act as a diaphragm that makes the ISFET die more sensitive to expansion and contraction of the o-ring. These stresses may lead to measurement errors.

In contrast to these existing pH sensors, pH sensor 4 includes o-ring 56 that is positioned over cap 42. This arrangement between o-ring 56 and cap 42 may reduce stress on ISFET die 10 generated by relative expansion and contraction between o-ring 56 and ISFET die 10 by eliminating direct contact between o-ring 56 and ISFET die 10. In one example, o-ring 56 may seal cap 42 with the outer housing (FIG. 1). In such an example, o-ring 56 may couple to a cover member or to a portion of header 60.

In some examples, the pH output signal (for example, signal indicative of pH level 19) of pH sensor 4 may be subject to repeatable errors due to pressure and temperature changes. For example, as discussed above, pH sensor 4 may undergo strain from the temperature and pressure changes, which may affect the performance of sensor 4. While features of sensor 4 help minimize the strain, e.g., by isolating ISFET die 10 from substrate 40 with frit material 40, these sensor errors may still lead to a non-linearity in the calculated pH. Some of these errors may be compensated for or corrected using a correction algorithm to adjust the pH output signal for the effects of pressure and temperature changes. In some examples, a polynomial correction algorithm is used to correct for the non-linearity in the pH. In some examples, non-correctable errors, such as hysteresis and non-repeatability, are reduced by locating o-ring 56 over cap 42 (as opposed to having an o-ring 56 in contact with ISFET die 10).

Figure 4A:
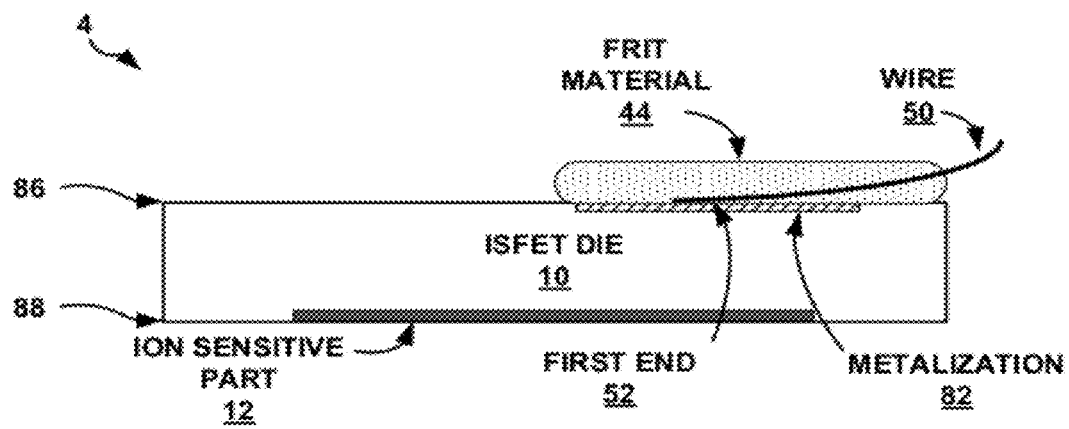
FIGS. 4A-4C are block diagrams illustrating one example of a pH sensor at various stages of manufacture, in accordance with one or more aspects of the present disclosure.
Figure 4B:
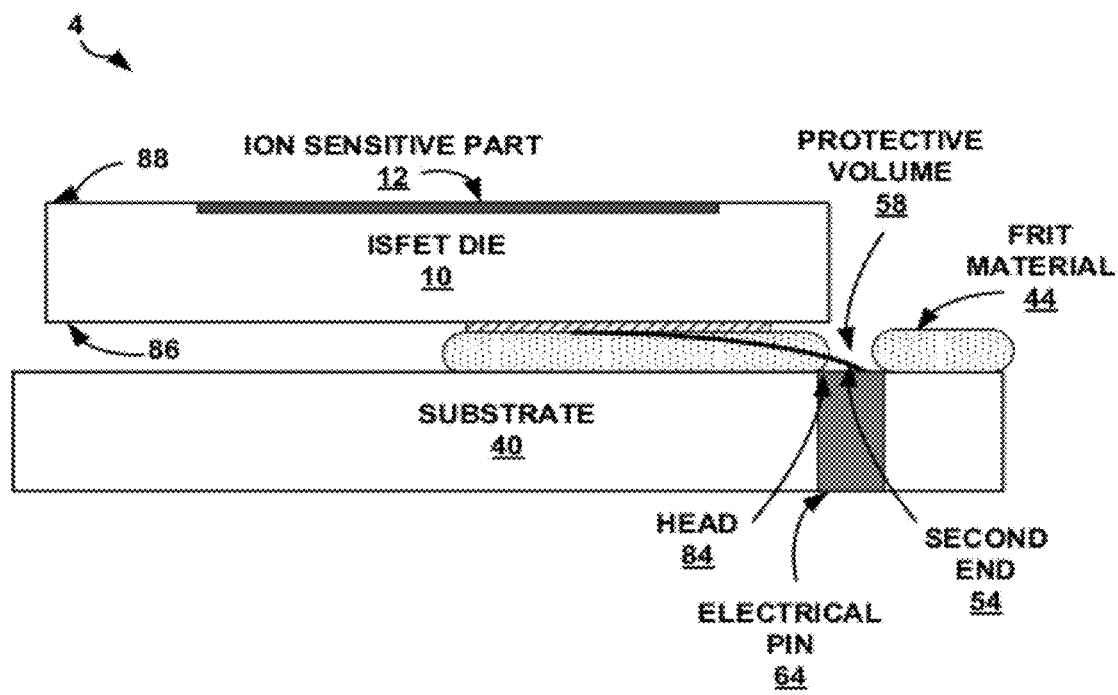
Figure 4C:
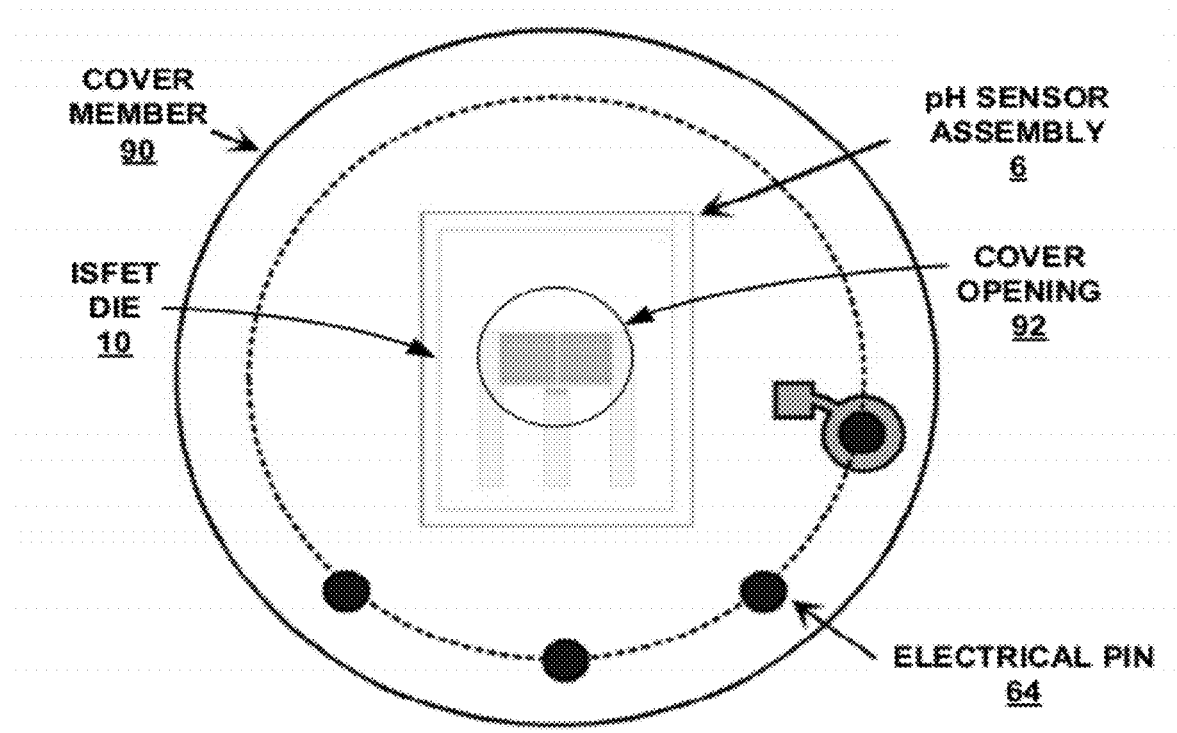

In some examples, substrate 40 may be mounted to header 60. In one example, an epoxy mount 62 is used to mount substrate 40 to header 60. However, in other examples, other forms or techniques for mounting substrate 40 to header 60 are used. As shown in the example of FIG. 2, header 60 may contain one or more electrical pins 64. In one example, electrical pins 64 extend beyond header 60. In other examples, header 60 may be part of pH sensor housing 8 for pH sensor assembly 6. Additionally, pH sensor housing 8 may further comprise a cover member 90 (as shown in FIG. 4C) that seals with o-ring 56 and mechanically couples to header 60.

Any of the layers as described herein with respect to FIG. 2 (such as substrate 40 or protective layer 14, for example)

may be a single layer or a structure of more than one layer or partial layers. Furthermore, any of the layers or structures described in example of FIG. 2 may be combined with other layers or structures in additional examples. ISFET die 10 may also have additional layers or structures. In further examples, the layers of pH sensor 4 may have any type of structure, for example, polycrystalline, monocrystalline, amorphous, or the like.

Figure 3:
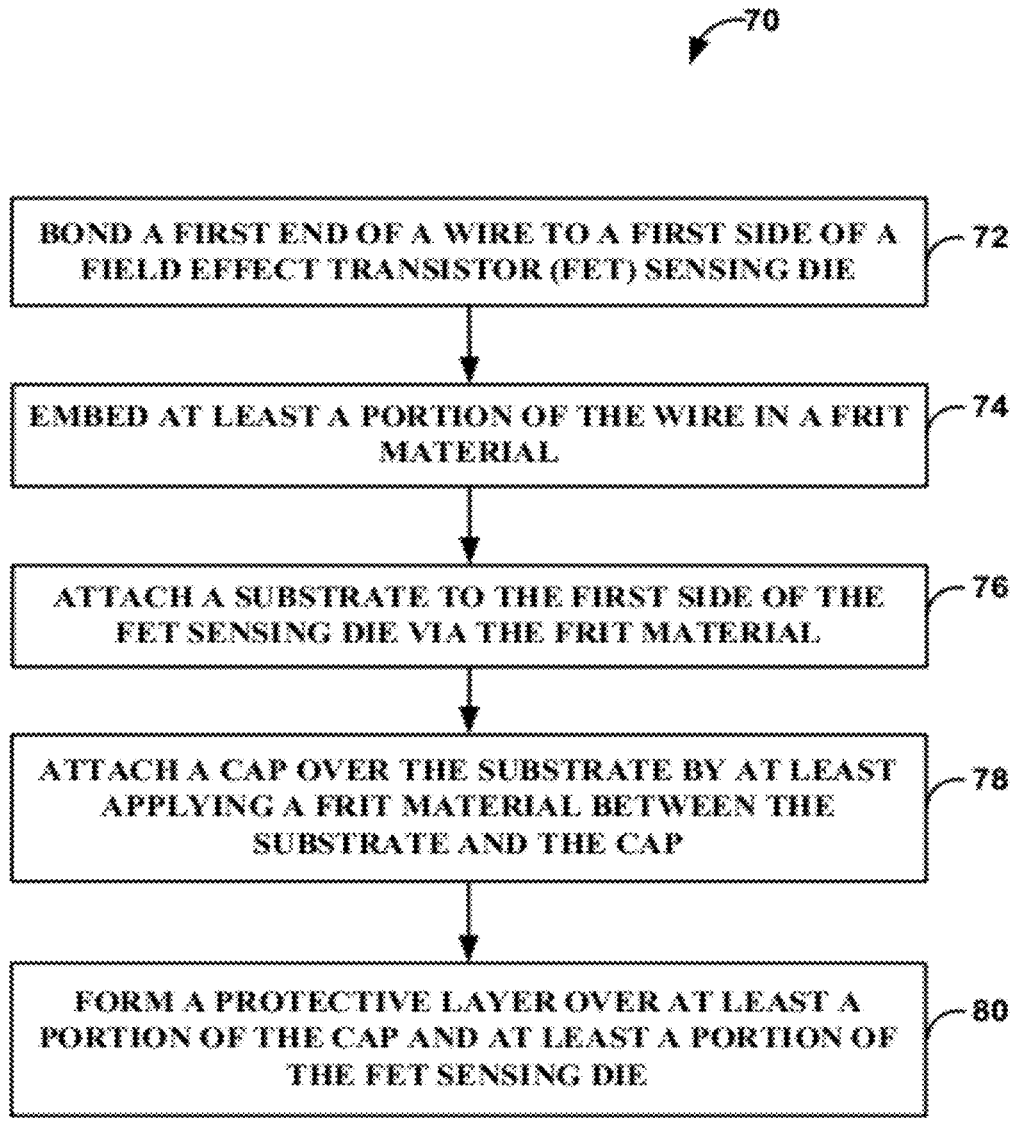
FIG. 3 is a flowchart illustrating an example method for manufacturing a pH sensor comprising a protective layer, in accordance with one or more aspects of the present disclosure.

FIG. 3 is a flowchart illustrating an example method 70 for manufacturing a pH sensor comprising a protective layer, in accordance with one or more aspects of the present disclosure. As discussed herein, method 70 is described with respect to the examples of pH sensor 4 described with respect to FIGS. 1, 2, and 4A-4C. However, method 70 may apply to other sensor examples of the present disclosure as well. Method 70 may be partially illustrated by FIGS. 4A-4C, which are described herein in conjunction with FIG. 3. FIGS. 4A-4C are block diagrams illustrating one example of a pH sensor 4 at various stages of manufacture, in accordance with one or more aspects of the present disclosure.

In the example shown in FIG. 3, method 70 comprises bonding a first end of a wire to a first side of a field effect transistor (FET) sensing die (72). In some examples, method 70 may also comprise embedding at least a portion of the wire in a frit material (74). In some examples, the frit material comprises a glass frit, wherein a thermal coefficient of expansion of the glass frit approximately matches a thermal coefficient of expansion of the ISFET die.

Turning briefly to FIG. 4A, a first end 52 of wire 50 may be bonded to a metallization 82 on a first side 86 of ISFET die 10 (72). Metallization 82 may be any metallization pad used to make an electrical connection between ISFET die 10 and an external device (e.g., processors 22 shown in FIG. 1). Wire 50 may be bonded to metallization 82 using any of the techniques for wire bonding currently known or later developed, such as by soldering wire 50 to metallization 82. As shown in FIG. 4B, first side 86 of ISFET die 10 is a side of ISFET die 10 that may be bonded to substrate 40 via frit material 44. A second side 88 of ISFET die 10 may be opposite first side 86, wherein ion sensitive part 12 may be located. In one example, ion sensitive part 12 may be able to be exposed to a media of interest to determine a pH of the media.

Once wire 50 is bonded to metallization 82, frit material 44 may be added to the pH sensor 4 (74). In some examples, some frit materials 44 used for wafer bonding may be deposited by screen printing techniques, wherein frit material 44 may be deposited as a paste. In one example, the paste contains a particulate glass frit material, such as a thixotropic binder, and a solvent for the binder. The proportions of frit material 44, binder, and solvent may be adjusted to allow screen printing of a controlled volume of the paste on a designated bonding surface of one of the wafers (for example, on substrate 40 or cap substrate 42). Thus, frit material 44 may be applied to ISFET die 10 using silkscreen techniques, or any other suitable technique for applying frit material now known or later developed. In one example, at least a portion of wire 50 is fed through frit material 44 such that the portion of wire 50 is embedded in frit material 44.

Frit material 44 may be placed in a heater (such as, but not limited to, a belt furnace), to harden frit material 44 in some examples. Firing frit material 44 may be performed in a single step, or in two or more steps. One example two step process comprises first performing a firing in order to drive out any volatiles in frit material 44 (such as solvents and binders, for example). Second, another firing is performed to melt frit material 44. A rigid structure of frit material 44 may be left once frit material 44 cools. In one example, this two-step firing process is performed with one or more wires 50 embedded in frit material 44. As shown in the example of FIG. 4A, the wire bonding at first end 52 of wire 50 is encased in frit material 44. This seals the electrical connection between wire 50 and metallization 82 and provides structural integrity to wire 50. Frit material 44 is also melted around edges of ISFET die 10 to provide electrical isolation from stray currents.

Returning to FIG. 3, method 70 may further include attaching a substrate to the first side of the FET sensing die via the frit material (76). Method 70 may also include bonding a second end of the wire to a head of at least one header pin, wherein the header pin extends through the substrate. As shown in FIG. 4B, ISFET die 10 may be mounted to substrate 40 via frit material 44, which substantially fixes the position of ISFET die 10 relative to substrate 40 following hardening of frit material 44 (e.g., using the techniques described above). In one example, attaching substrate 40 to first side 86 of ISFET die 10 further comprises melting frit material 44.

Additionally, after a portion of wire 50 is embedded in frit material 44, a second end 54 of wire 50 may be bonded to a head 84 of an electrical pin 64. In some examples, a protective volume 58 is formed over the wire bond of second end 54 of wire 50 in order to reduce stress effects on the wire bond. In some examples, protective volume 58 does not contain frit material 44. Protective volume 58 above electrical pin 64 decreases a chance that any mismatch between a TCE of electrical pin 64 and frit material 44 may exert undesirable stresses on the wire bond. The undesirable stresses may, for example, affect the integrity of the wire bond, which may affect the performance of pH sensor 4. In some examples, protective volume 58 comprises a gas, a gas mixture, or a partial or full vacuum. Embedding at least a portion of wire 50 in frit material 44 results in a wire bond electrical connection that is encapsulated in frit material 44 except for protected volume 58 around head 84 of electrical pin 64. These features may protect the wire bonds from leakage currents and to external environmental effects.

Returning to FIG. 3, method 70 may further comprise attaching a cap over the substrate by at least applying a frit layer between the substrate and the cap (78). For example, cap 42 may be attached over substrate 40 via frit material 44. In one example, after an initial firing to harden frit material 44, a first wafer (e.g., base substrate 40) is aligned with and mated with a second wafer (e.g., cap substrate 42) so that frit material 44 contacts a complementary bonding surface of the second wafer. The wafers may then be incrementally heated to completely remove any solvent and binder from frit material 44 and to melt frit material 44. In one example, pressure is placed on ISFET die 10 in order to drive molten frit material 44 up the vertical sidewall region 70 in between ISFET die 10 and cap 42 (as shown with respect to the configuration of frit material 44 in FIG. 2). Upon cooling, in one example, frit material 44 re-solidifies to form a substantially homogeneous glass bond line between substrate 40 and cap 42. Thus, various bonding techniques using intermediate bonding materials, such as glass frit, may be used to improve the strength and reliability of the wafer bond.

Method 70 may also comprise forming a protective layer over at least a portion of the cap and at least a portion of the FET sensing die (80). For example, protective layer 14 may be formed over a portion of cap 42 and a portion of ISFET die 10. In one example, forming protective layer 14 further comprises applying a metal oxide pH media barrier over at least a portion of cap 42 and at least a portion of ISFET die 10. Any now known or later developed techniques, such as sputtering or other deposition, may be used to form protective layer 14. For example, in examples in which protective layer 14 is synthetic diamond, vapor cloud technology may be used to create diamond crystals on the desired surfaces. In an example in which protective layer 14 is sapphire, a fog method may be used to put down a sapphire coating. In other examples, protective layer 14 may be a ceramic layer that is flame sprayed over the desired surfaces.

Method 70 may also comprise mounting substrate 40 on a pressure isolation device (such as header 60). Seals may be formed where the at least one header pin extends through the pressure isolation device, for example, a glass-to-metal seal.

In other examples, method 70 further comprises attaching a cover member, over at least a portion of the cap. As shown in FIG. 4C, which is a schematic top view of pH sensor assembly 6, a cover member 90 houses pH sensor assembly 6. Cover member 90 may also comprise a cover opening 92 that is located over ISFET die 10. In some examples, cover opening 92 comprises an opening that is positioned proximate to ion sensitive part 12 of ISFET die 10. Cover opening 92 allows ion sensitive part 12 to be exposed to a media. In one example, cover member 90 couples to protective layer 14 via o-ring 56. In that case, no portion of cap 42 or frit material 44 may be exposed to the media. In some examples, header 60 and cover member 90 comprise a single device.

In another example, method 70 may also comprise forming a protective volume around the head of an electrical pin when bonding the second end of the wire to the head of the electrical pin. This protective volume (such as protective volume 58) may be a space in pH sensor assembly 6 that does not have any frit material 44. In one example, protective volume 58 allows pH sensor 4 to expand and contact while minimizing strain exhibited at the wire bond between second end 54 of wire 50 and head 84 of electrical pin 64. Protective volume 58 may partially overlap electrical pin 64.

As described herein, a wire bond may be encapsulated in a glass frit in a sensing device in order to improve stress isolation. Because exposing glass frit to media such as seawater may leach heavy ions out of the glass frit, which may cause the glass frit to leak or result in other affects to the integrity of the glass frit, a protective coating or layer is formed on a top of a sensor die to help protect the glass frit from the media. In one example, the protective coating is a metal oxide. In some examples, mounting materials used to form the pH sensor assembly have a TCE that is close to a TCE of an ISFET die, to reduce stresses from disparate expansion or contraction.

In the discussion and claims herein, the term "on" used with respect to two materials, one "on" the other, means at least some contact between the materials, while "over" means the materials are in proximity, but possibly with one or more additional intervening materials such that contact is possible but not required. Neither "on" nor "over" implies any directionality as used herein. The term "about," "approximate," or the like indicates that the value listed may be somewhat altered, as long as the alteration does not result in nonconformance of the process or structure to the illustrated example.

Terms of relative position as used in this disclosure are defined based on a plane parallel to the conventional plane or working surface of a wafer or substrate, regardless of the orientation of the wafer or substrate. The term "horizontal" as used in this disclosure is defined as a plane parallel to the conventional plane or working surface of a wafer or substrate, regardless of the orientation of the wafer or substrate. The term "vertical" refers to a direction perpendicular to the horizontal. Terms such as "on," "side" (as in "sidewall"), "higher," "lower," "over," "top," and "under" are defined with respect to the conventional plane or working surface being on the top surface of the wafer or substrate, regardless of the orientation of the wafer or substrate.

Various aspects of the disclosure have been described. Aspects or features of examples described herein may be combined with any other aspect or feature described in another example. These and other examples are within the scope of the following claims.

The invention claimed is:

1. A pH sensor comprising:
   a substrate including a base substrate and a cap formed over the base substrate;
   an ion sensitive field effect transistor (ISFET) die comprising an ion sensing part that responds to pH, wherein the ISFET die is located over the substrate;
   a protective layer formed over at least a first portion of an outer surface of the ISFET die and at least a portion of the substrate, wherein the protective layer is not formed over at least a second portion of the outer surface of the ISFET die;
   a frit material formed at least partially in a sidewall region between the ISFET die and the cap, wherein the protective layer is formed over at least a portion of the frit material in the sidewall region and over at least a portion of the cap; and
   a cover member mechanically coupled to the protective layer, wherein the cover member houses the ISFET die and the substrate, and wherein the cover member defines an opening proximate to the ion sensing part.

2. The pH sensor of claim 1, wherein a thermal coefficient of expansion of the ISFET die approximately matches a thermal coefficient of expansion of the frit material.

3. The pH sensor of claim 1, further comprising:
   at least one wire, wherein a first end of the at least one wire is bonded to the ISFET die, wherein a portion of the wire is embedded in the frit material.

4. The pH sensor of claim 3, further comprising:
   at least one electric pin, wherein a second end of the at least one wire is bonded to the at least one electric pin.

5. The pH sensor of claim 4, wherein the at least one wire is bonded to the at least one electric pin within a protective volume formed in the frit material.

6. The pH sensor of claim 1, further comprising:
   an o-ring coupled between the protective layer and the cover member.

7. The pH sensor of claim 1, wherein the protective layer comprises a metal oxide, synthetic diamond, sapphire, or combinations thereof.

8. The pH sensor of claim 1, wherein the protective material comprises tantalum pentoxide, titanium oxide, silicon nitride, or combinations thereof.

9. The pH sensor of claim 1, further comprising:
   a header, wherein the substrate is mounted to the header;
   a reference electrode configured to provide a reference voltage; and
   at least one electric pin coupled to the ISFET die via a wire, wherein the wire is at least partially embedded in the glass frit,
   wherein the ISFET die is mounted to the substrate via the glass frit, and
   wherein the ISFET die is configured such that when the ion sensing part of the ISFET die is exposed to a medium, the ion sensing part outputs a signal related to a pH level of the medium.

10. A sensor device comprising:
    a substrate including a base substrate and a cap substrate formed over the base substrate;
    a field effect transistor (FET) die mounted over the substrate via a frit material, wherein the frit material is formed at least partially in a sidewall region between the FET die and the cap substrate;

a protective layer formed over at least a first portion of an outer surface of the FET die, at least a portion of the frit material in the sidewall region, and at least partially over the cap substrate, wherein the protective layer is not formed over at least a second portion of the outer surface of the FET die; and at least one wire that is bonded to the FET die at a first end, wherein at least a portion of the wire is embedded in the frit material.

11. The sensor device of claim 10, further comprising:

a cover member that houses the substrate, wherein the cover member defines an opening proximate to the FET die; and an o-ring positioned between the cover member and the protective layer.

12. The sensor device of claim 11, wherein a portion of the protective layer and the second portion of outer surface of the FET die are exposed by the opening defined by the cover member.

13. The sensor device of claim 10, wherein the protective layer comprises tantalum pentoxide, titanium oxide, synthetic diamond, sapphire, silicon nitride, or combinations thereof.

14. The sensor device of claim 10, wherein the outer surface of the FET die is approximately flush with an outer surface of the cap substrate.

15. The sensor device of claim 10, wherein the protective layer comprises a non-porous material.

\* \* \* \* \*